United States Patent
Smith

[11] Patent Number: 6,056,764
[45] Date of Patent: May 2, 2000

[54] OPTHALMIC SURGICAL BLADE HAVING HARD SINGLE BEVEL EDGES

[76] Inventor: Thomas C. Smith, 13125 Wilcox Rd., Largo, Fla. 33774

[21] Appl. No.: 09/040,800

[22] Filed: Mar. 18, 1998

[51] Int. Cl.[7] .................................................. A61B 17/32
[52] U.S. Cl. ........................... 606/167; 606/166; 606/107
[58] Field of Search ...................... 606/166, 167, 606/107, 185, 161, 79

[56] References Cited

U.S. PATENT DOCUMENTS

| | | | |
|---|---|---|---|
| 4,720,918 | 1/1988 | Curry et al. | 30/346.55 |
| 5,201,747 | 4/1993 | Mastel . | |
| 5,203,865 | 4/1993 | Siepser . | |
| 5,217,476 | 6/1993 | Wishinsky . | |
| 5,222,967 | 6/1993 | Casebeer et al. . | |
| 5,352,233 | 10/1994 | Anis . | |
| 5,370,652 | 12/1994 | Kellan . | |
| 5,376,099 | 12/1994 | Ellis et al. . | |
| 5,423,840 | 6/1995 | Casebeer et al. . | |
| 5,619,889 | 4/1997 | Jones et al. | 76/104 |
| 5,713,915 | 2/1998 | Van Heugten et al. | 606/167 |

FOREIGN PATENT DOCUMENTS

| | | | |
|---|---|---|---|
| 1424-814-A | 9/1988 | Russian Federation | 606/167 |

OTHER PUBLICATIONS

Apr. 1997, McFarland, Why Scleral Tunnel Incisions Aren't Passe.
Apr. 1997, Hoffer, Try Oblique Corneal Incisions.
Apr. 1997, Fish, An Alternative to Clear Cornea.
Apr. 1997, Connor, Temporal Limbal Incisions.
Apr. 1997, Langerman, The Right Way To Do Hinge Incisions.
Apr. 1997, Ernest, A Corneal Incision You Can Be Comfortable With.

*Primary Examiner*—Michael Buiz
*Assistant Examiner*—Jennifer Maynard
*Attorney, Agent, or Firm*—Dennis G. LaPointe; Joseph C. Mason, Jr.

[57] ABSTRACT

A blade has a proximal end and a distal end and a central axis of elongation. The proximal end is generally rectangular cubic with a flat profile having top and bottom surfaces and short sidewalls, with each sidewall made up of two edges meeting to define an angle of approximately 100° to 140°. The apex of this angle is unsharpened and these sidewalls comprise guide means for guiding movements of the blade through an opening created by the cutting surfaces located on the distal end thereof. The distal end of the blade includes a cutting surface made up of a sharp pointed tip with the cutting edges proximal of the tip defining an angle of 75° to 85°. Two angled surfaces extend laterally and proximally to either side of the tip, each making an angle of 22° to 27° with the bottom surface of the blade. The tip is located between the planes defined by the top and bottom surfaces of the blade. The inventive blade is made from diamond. However, materials such as stainless steel, sapphire, ruby, cubic zirconia, pure or composite ceramics, ceramic metal composites, and titanium alloys can be substituted for the diamond.

17 Claims, 3 Drawing Sheets

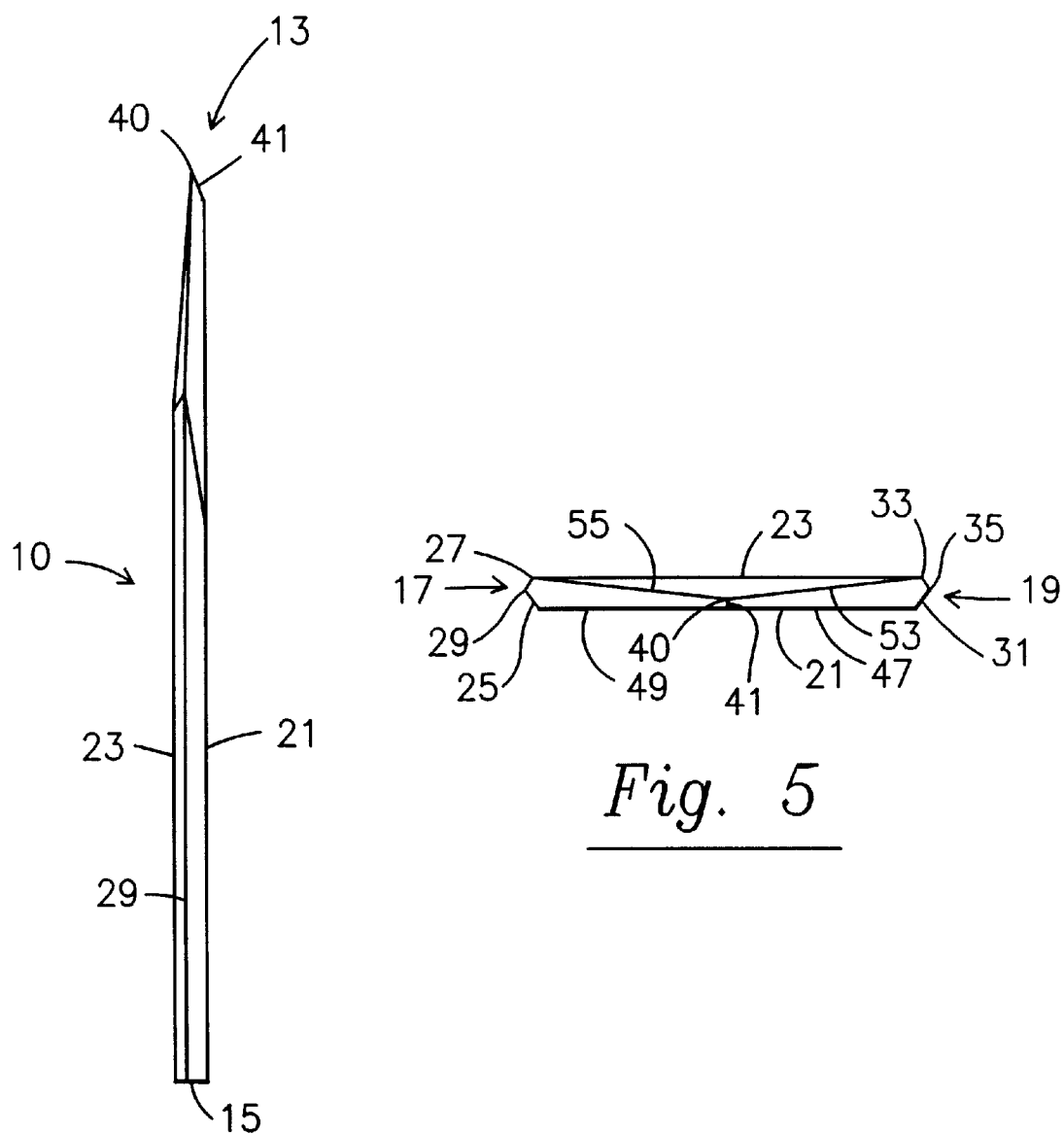

ic metal composites, and titanium alloys can be substituted for the diamond.

OPTHALMIC SURGICAL BLADE HAVING HARD SINGLE BEVEL EDGES

BACKGROUND OF THE INVENTION

The present invention relates to an ophthalmic surgical blade having hard single bevel edges. Performance of eye surgery using an ophthalmic surgical blade has become commnonplace. Numerous diverse blade designs are employed in such surgeries and each blade has its advantages and disadvantages.

During the performance of eye surgery, several problems arise caused by various features of prior art blades. For example, it is important to create a geodesic incision through the cornea at the proper angle and with the required pressure to facilitate self sealing characteristics of the wound. It is desirable, when making such an incision, to avoid deformation of eye tissues and to prevent inadvertent tearing or widening of the extremities of the incision such as are caused by sharp or squared sides on the width of the blade. Additionally, a blade should be able to create a self-sealing wound such as would be created when individual corneal layers are gradiently cut rather than slashed by the blade. A contoured cut properly aligns itself while a straight slash cut does not do so.

The following prior art is known to Applicant:

U.S. Pat. No. 5,217,476 to Wishinsky discloses a surgical knife blade and method of performing cataract surgery utilizing a surgical knife blade. While embodiments of the Wishinsky knife blade, particularly those shown in FIGS. 1–5, are symmetrical, the present invention distinguishes from the teachings of Wishinsky as contemplating a blade wherein the lateral surfaces thereof are unsharpened and merely act as guide means.

U.S. Pat. No. 5,222,967 to Casebeer et al. discloses a keratorefractive diamond blade and surgical method wherein the blade is asymmetrical about a central longitudinal axis. The same may be said for U.S. Pat. No. 5,423,840, also to Casebeer et al. The present invention differs from the teachings of these patents as contemplating an ophthalmic blade that is symmetrical about a central longitudinal axis and has side surfaces that are not sharpened but, rather, merely function as guide means.

U.S. Pat. No. 5,352,233 to Anis discloses a scalpel and technique for using scalpel including one embodiment showing a blade that is symmetrical about a longitudinal axis of elongation thereof. This embodiment shows sharp corners at the widest portions of the blade and a blade edge that is equidistant from the top and bottom surfaces of the blade. The present invention differs from the teachings of Anis as having side edges that are not sharpened and that merely perform a guiding function as well as a sharpened edge that is not equidistant from the top and bottom surfaces of the blade.

U.S. Pat. No. 5,370,652 to Kellan discloses a surgical knife blade for making sutureless incisions in the eye and methods therefor. The blades of Kellan are symmetrical with respect to a longitudinal axis of elongation thereof. In one embodiment, the blade edge includes a sharpened central point and side edges that are sharp as well. Other embodiments include curved cutting surfaces wherein a central point is not included. In each embodiment, the cutting edge is in a plane common with the bottom surface of the blade. The present invention differs from the teachings of Kellan as contemplating a blade symmetrical with respect to a longitudinal axis of elongation thereof having a central point, side edges that are not sharpened and merely provide guiding surfaces, and wherein the cutting edge is not equidistantly located between the top and bottom surfaces of the blade and is not in any plane common with either of those surfaces.

U.S. Pat. No. 5,376,099 to Ellis et al. discloses an undercut diamond surgical blade and method of using same. Embodiments of Ellis et al. include cutting surfaces on a blade sidewall and a cutting edge equidistantly spaced between the top and bottom surfaces thereof. In contrast, the present invention contemplates a blade having a pointed end aligned with an axis of elongation thereof with side edges unsharpened and comprising guide means and with the cutting edge being non-equidistantly spaced between the top and bottom surfaces thereof.

SUMMARY OF THE INVENTION

The present invention relates to an ophthalmic surgical blade having hard single bevel edges. The present invention includes the following interrelated objects, aspects and features:

(1) In a first aspect, the inventive blade has a proximal end and a distal end and a central axis of elongation. The proximal end is generally rectangular cubic with a flat profile having top and bottom surfaces and short sidewalls, with each sidewall made up of two edges meeting to define, therebetween, an angle of approximately 100° to 140°. The apex of this angle is unsharpened and these sidewalls comprise guide means for guiding movements of the blade through an opening created by the cutting surfaces located on the distal end thereof.

(2) The distal end includes a cutting surface made up of a plurality of interrelated edges and facets. The distal end of the blade defines a sharp pointed tip with the cutting edges proximal of the tip defining an angle of 75° to 85°. An edge extends from the tip a short distance proximally aligned with the central axis of elongation, and two angled surfaces extend laterally and proximally to either side of this edge with these surfaces having distal edges that define the 75° to 85° angle described above. These distal edges extend proximally from the absolute distal tip of the blade to termination points coinciding with a bottom surface of the blade. The absolute distal tip is located between the planes defined by the top and bottom surfaces of the blade. The proximal termination of the edge described above as extending along the longitudinal axis of elongation of the blade comprises the distal point of termination of proximal edges of the two angled surfaces, which proximal edges extend distally to termination points on the top surface of the blade.

(3) These proximal edges of the blade define therebetween a first generally triangular surface and the distal edges of the blade define a second generally triangular surface. In the preferred embodiment of the present invention, the first generally triangular surface is coplanar with the top surface of the blade. The first generally triangular surface makes an angle with the second generally triangular surface of approximately 3° to 5°. Looking at the angled surfaces, each of which is, in part, defined by a proximal edge and a distal edge, these angled surfaces make an angle with the bottom surface of the blade of approximately 22° to 27° with the range of 25° to 27° being preferred.

(4) In the preferred embodiment of the present invention, the blade has a width of 1.0 to 4.0 millimeters and a thickness of from 150 to 250 microns.

(5) The inventive blade may be made from diamond, however, materials such as stainless steel, sapphire, ruby, cubic zirconia, pure or composite ceramics, ceramic metal composites, and titanium alloys can be substituted for the diamond.

(6) In the preferred embodiment, where the material from which the blade is made of metal, the blade is suitably coated on both sides with a material that is dissimilar to the blade material but harder than the blade material. The coating should have zero porosity, strong adhesion to the substrate surface, fracture resistance, insolubility in typical cleaning solutions, and non-reactivity with respect to body tissues and chemicals. The coating material should be sufficiently resilient, corrosion resistant and biocompatible. The coating on the surgical blade may be applied by chemical or physical vapor deposition, flame deposition or lamination with heat and pressure after which the blade is sharpened on one side of each edge only. The cutting edge is then composed of the hard coating honed to a sub-micron edge radius of less than 0.1 micron.

Accordingly, it is a first object of the present invention to provide an ophthalmic surgical blade having hard single bevel edges.

It is a further object of the present invention to provide such a blade having a cutting tip with cutting edges emanating therefrom defining an angle in the range of 75° to 85°.

It is a further object of the present invention to provide such a blade wherein beveled surfaces emanating proximally from the tip have surfaces defining an angle of between 22° to 27° with respect to a bottom surface of the blade.

It is a still further object of the present invention to provide such a blade having an approximate thickness of 150 to 250 microns and an approximate width of 1.0 to 4.0 millimeters.

It is a yet further object of the present invention to provide such a blade having side edges, each of which is made up of two surfaces meeting at an angle of between 100° to 140° at an unsharpened apex.

These and other objects, aspects and features of the present invention will be better understood from the following detailed description of the preferred embodiment when read in conjunction with the appended drawing figures.

BRIEF DESCRIPTION OF THE DRAWINGS

FIG. 4 shows an enlarged side view thereof, of which the other side is identical.

FIG. 5 shows a front view thereof.

SPECIFIC DESCRIPTION OF THE PREFERRED EMBODIMENT

Figure 1:
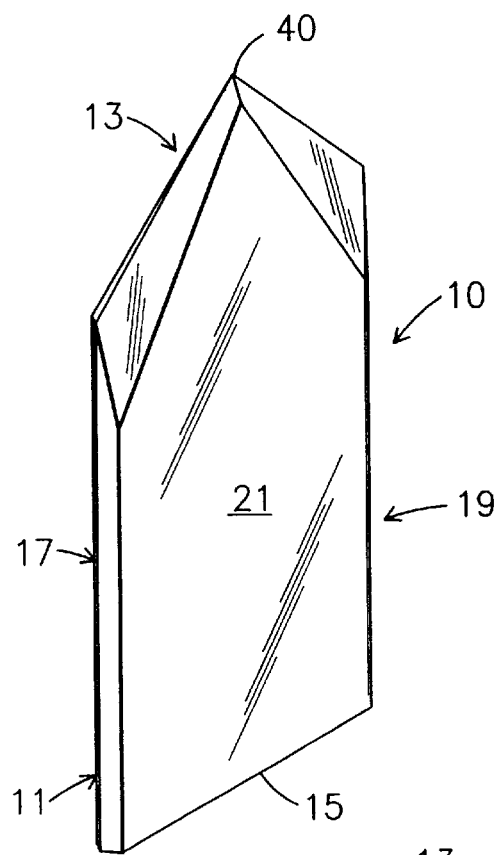
FIG. 1 shows a perspective view of the inventive blade.

With reference, first, to FIGS. 1–5, a blade in accordance with the teachings of the present invention is generally designated by the reference numeral 10 and is seen to include a proximal end 11 and a distal end 13. The proximal end 11 is generally rectangular cubic having a proximal end surface 15, side edges 17 and 19, a top surface 21 and a bottom surface 23.

With particular reference to FIG. 5, the side edges 17 and 19 are each composed of two angled surfaces. Thus, the side edge 17 includes an upper surface 25 and a lower surface 27 that meet an unsharpened elongated linear apex 29. The side edge 19 similarly includes an upper surface 31 and a lower surface 33 that meet at an unsharpened elongated linear apex 35.

The distal end 13 of the blade 10 includes a distal pointed tip 40 that is located "in space" between planes defined by the top surface 21 and the bottom surface 23. An edge 41 extends proximally in alignment with the central axis of elongation of the blade 10 from the tip 40 to a proximal termination thereof 43 that lies in the plane of the top surface 21 and forms the apex of a triangular surface 45 defined by proximal edges 47 and 49 and the dotted line 51. The surface 45 is coplanar with and extends from the top surface 21.

Figure 2:
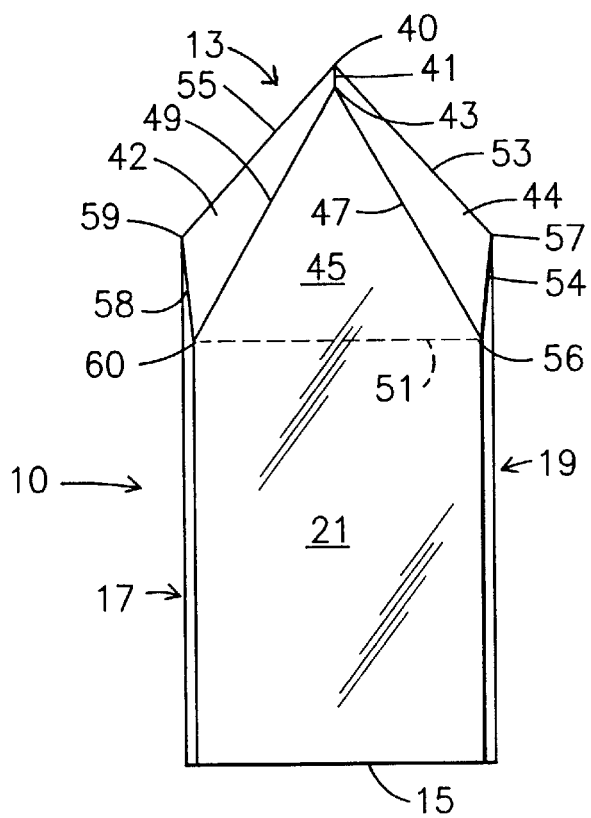
FIG. 2 shows a top view of the inventive blade.
Figure 3:
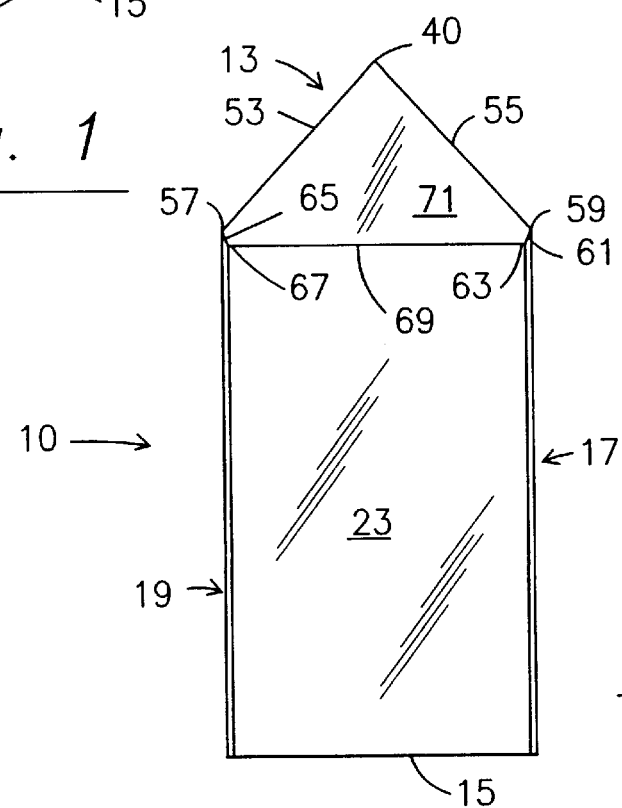
FIG. 3 shows a bottom view thereof.

With further reference to FIGS. 1 and 2, the distal tip 40 is defined, in part, by distal edges 53, 55 that have respective proximal terminations 57 and 59, respectively. A segment 58 (FIG. 2) extends proximally from the point 59 to a termination 60 at the left termination of the dotted line 51. A segment 54 (FIG. 2) extends proximally from the point 57 to a point 56 forming the right-hand termination of the dotted line 51. The edge 41 along with the edges 55, 49 and the segment 58 form a first angled surface 42 whereas the edge 41 along with the edges 53 and 47 and the segment 54 form a second angled surface 44. The proximal termination 59 connects to a short segment 61 (FIG. 3) having a proximal termination at 63 that lies in the plane of the bottom surface 23. Similarly, a short segment 65 (FIG. 3) interconnects between the proximal termination 57 of the edge 53 and a point 67 lying in the plane of the bottom surface 23. The points 63 and 67 are interconnected by the line 69 shown in FIG. 3 such that a second generally triangular surface 71 is defined by the edges 53, 55, 61, 65 and the line 69.

In the preferred embodiment of the present invention, the following specifications and dimensions are followed:

(1) The surfaces 42 and 44 each make an angle with respect to the bottom surface 23 and generally triangular surface 71 of approximately 22° to 27° with the range of 25° to 27° being preferred.

(2) The plane of the generally triangular surface 45 defines an angle with the plane of the generally triangular surface 71 of approximately 3° to 5°.

(3) The edges 53 and 55 make an angle therebetween as defined at the distal termination point 40 of 75° to 85°.

(4) Concerning the side edges 17 and 19, the surfaces 25 and 27 form an angle therebetween of 100° to 140° with an angle of 120° being preferred. Similarly, the surfaces 31 and 33 form an angle therebetween of 100° to 140° with an angle of 120° being preferred.

(5) The preferred width of the inventive blade 10 between the apices 29 and 35 is 1.0 to 4.0 millimeters.

(6) The thickness of the inventive blade 10 between the top surface 21 and the bottom surface 23 is from 150 to 250 microns.

The inventive blade 10 may be made of any suitable material including, for example, diamond, stainless steel, sapphire, ruby, cubic zirconia, pure or composite ceramics, ceramic metal composites and titanium alloys.

In the preferred embodiment, where the material from which the blade is made is metal, i.e., stainless steel or Titanium, the blade is suitably coated on both sides with a material that is dissimilar to the blade material but harder than the blade material. The coating should have zero porosity, strong adhesion to the substrate surface, fracture resistance, insolubility in typical cleaning solutions, and non-reactivity with respect to body tissues and chemicals. The coating material should be sufficiently resilient, corrosion resistant and biocompatible. The coating on the surgical blade may be applied by chemical or physical vapor deposition, flame deposition, sputtering, molecular beam epitaxy or lamination with heat and pressure after which the blade is sharpened on one side of each edge only. The tip of the cutting edge is then composed of the hard coating honed to a sub-micron edge radius of less than 0.1 micron.

The coating that may be applied to a metallic blade substrate may be any one of the following: titanium nitride, titanium carbide, titanium carbide-nitride, high purity chrome, diamond-like carbon, aluminum oxide, boron nitride, silicon carbide or silicon nitride. Where the substrate is made of stainless steel or titanium, it is sometimes appropriate to provide the coating in two layers. Thus, in this example, it might be appropriate to first coat a layer of titanium carbide on the metal substrate and, thereafter, apply a coating of diamond-like material over the titanium carbide layer.

A preferred method employed to hone the precise edge on the blade is to secure the blade in a holding fixture at a fixed or adjustable angle and/or index. The blade edge is then lowered onto a lapping wheel, consisting of a rotating disk, the contact surface of which contacts or bears a substance that by abrasion, plastic flow, chemical dissolution, or any combination thereof removes both the coating and substrate. The rate of removal of both coating and substrate should be similar. The cutting edge of the blade may be oriented perpendicular into the disk or obliquely into the disk, during honing. The holding fixture should exert just enough pressure on the cutting edge to keep the blade from skipping, but not so much pressure as would cause fracture of the cutting edge or bending of the blade. The lapping unit should be set up to minimize vibrations exerted on the blade from the cutting disk and holding fixture by using a precisely ground lapping disk and fixturing devoid of play in the fastened and moving parts. The lapping disk may be used such that the blade is lapped on the flat side, outer diameter or inner diameter.

The cutting edges should preferably be lapped to a minimum standard of 50x magnification chip-free under transmitted light in order to be acceptable for precise surgical applications. The blade is initially examined at 10 to 20x magnification to monitor and adjust the orientation of the blade edge on the disk. Then, when correct orientation is achieved, the edges are lapped and checked under an inspection scope at 50x magnification or higher.

The edge sharpening is completed when it meets these required specifications. After all edges have been suitably lapped, the blade is taken out of the lapping fixture, cleaned to remove residual chemicals, abrasive dust, and grinding swarf by rinsing with a solvent, gentle wiping with a soft, uniform material, or through ultrasonic cleaning.

Figure 7:
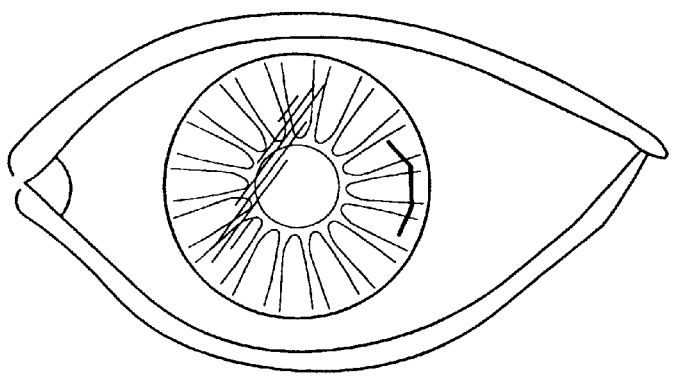
FIG. 7 shows a front view of an eye with a slit formed by a prior art blade formed therein.

FIG. 7 shows an incision 4 performed through the use of a prior art ophthalmic surgical blade. Of note is the arcuate frown-like shape of the incision 4.

Figure 6:
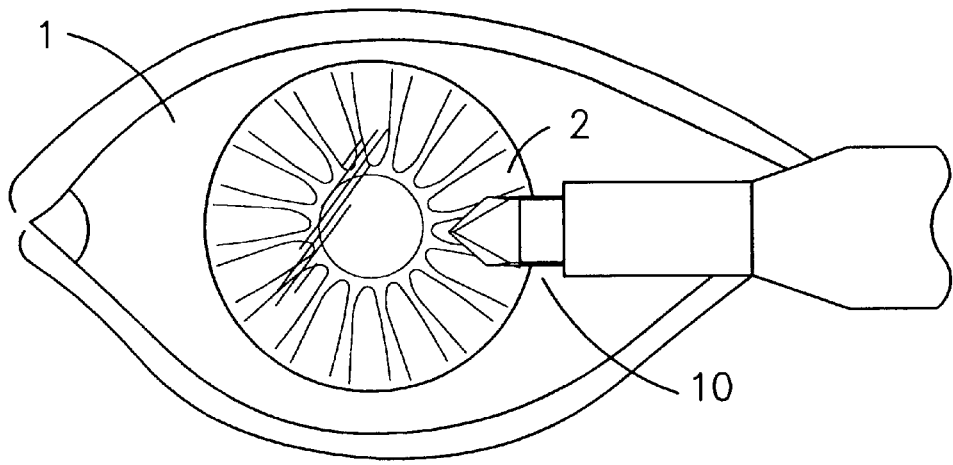
FIG. 6 shows a front view of an eye with the inventive blade cutting a slit therein.
Figure 8:
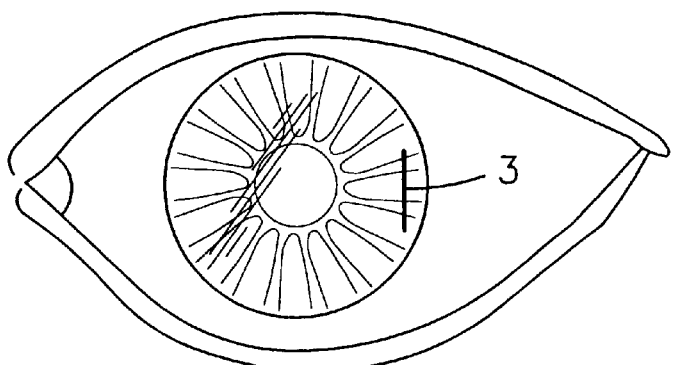
FIG. 8 shows a front view of an eye with a slit formed through the procedure illustrated in FIG. 6 being formed thereby.

FIG. 6 shows a blade in accordance with the teachings of the present invention inserted within the cornea 2 of an eyeball 1. The resultant incision 3 is depicted in FIG. 8 and, as is shown, is straight. In this regard, it should be understood that the unsharpened side edges 17, 19 merely guide movements of the blade 10 into and out of the incision formed by the distal end 13 thereof. These unsharpened side edges 17, 19 prevent deformation of the eye tissues, prevent inadvertent tearing or widening of the lateral extremities of the incision, and avoid tearing of the epithelial tissue. The triangular surface 45 coplanar with the top surface 21 provides a reference plane permitting the surgeon to make a straight incision. The triangular surface 71 slightly angled with respect to the bottom surface 23 provides a reference plane permitting cutting of a groove.

As compared to the prior art, the inventive blade 10 is thinner near the tip 40 making the initial incision less expansive than is the case with prior art blades. Unlike skewed facet-style blades with parallel sharp lengthwise sides, the inventive blade 10 with unsharpened sides 17 and 19 can easily be repaired by simply re-lapping the facets near the tip of the blade on the top and bottom, which facets comprise the generally triangular surfaces 45 and 71. There are no sharp edges that could be damaged or that would require re-lapping. Thus, re-sharpening of the inventive blade does not result in loss of blade width. Use of the hard coating on a metal substrate dramatically increases blade life from the usual two to six uses before disposal.

As such, an invention has been disclosed in terms of a preferred embodiment thereof which fulfills each and every one of the objects of the invention as set forth hereinabove and provides a new and useful ophthalmic surgical blade having hard single bevel edges of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. An ophthalmic surgical blade, comprising:
   a thin elongated body having a proximal end and a distal end and a central axis of elongation;
   b) said proximal end including top and bottom flat parallel surfaces;
   c) said distal end having a single beveled edge blade portion including:
      i) a sharp tip lying in alignment with said axis of elongation and lying between said top and bottom surfaces;
      ii) cutting edges extending laterally and proximally from said tip, said cutting edges defining an angle therebetween of 75° to 85°;
      iii) angled cutting surfaces extending proximally from said cutting edges and extending proximally toward said top surface, each of said cutting surfaces defining an angle with said bottom surface of 22° to 27°;
      iv) a generally triangular surface extending from an apex at said tip and proximally diverging to a location of merger with said bottom surface, said generally triangular surface defining an angle with said top surface of 3° to 5°;
   d) said body having unsharpened side edges including two elongated guide surfaces meeting at an unsharpened apex, said guide surfaces defining an angle of 100° to 140°.

2. The blade of claim 1, wherein said cutting edges define an angle therebetween of 80°.

3. The blade of claim 1, wherein each of said cutting surfaces defines an angle with said bottom surface of 25° to 27°.

4. The blade of claim 1, wherein said top surface includes a further generally triangular surface extending from an apex just proximal of said tip and proximally diverging therefrom.

5. The blade of Claim 1, wherein said angle between said guide surfaces is 120°.

6. The blade of claim 1, wherein said proximal end of said blade is rectangular cubic.

7. The blade of claim 1, wherein said top and bottom surfaces are spaced apart a distance of 150 to 250 microns.

8. The blade of claim 1, wherein said side edges are spaced apart a distance of 1.0 to 4.0 millimeters.

9. The blade of claim 1, made of either stainless steel or a titanium alloy.

10. The blade of claim 9, including a coating chosen from the group consisting of titanium nitride, titanium carbide, titanium carbide-nitride, chrome, aluminum oxide, boron nitride, silicon carbide and silicon nitride.

11. The blade of claim 1, made of stainless steel.

12. The blade of claim 1, made of a material chosen from the group consisting of diamond, sapphire, ruby, cubic zirconia, and pure or composite ceramics.

13. An ophthalmic surgical blade, comprising:
 a) a thin elongated body having a proximal rectangular cubic end and a distal end and a central axis of elongation;
 b) said proximal end including top and bottom flat parallel surfaces spaced apart 150 to 250 microns;
 c) said distal end having a single beveled edge blade portion including:
  i) a sharp tip lying in alignment with said axis of elongation and lying between said top and bottom surfaces;
  ii) cutting edges extending laterally and proximally from said tip, said cutting edges defining an angle therebetween of 80°;
  iii) angled cutting surfaces extending proximally from said cutting edges and extending proximally toward said top surface, each of said cutting surfaces defining an angle with said bottom surface of 25° to 27°;
  iv) a generally triangular surface extending from an apex at said tip and proximally diverging to a location of merger with said bottom surface, said generally triangular surface defining an angle with said top surface of 3° to 5°;
 d) said body having unsharpened side edges comprising guide means for guiding cutting movements of said tip, each of said side edges including two elongated guide surfaces meeting at an unsharpened apex defining an angle of 120°, said apices being spaced apart 1.0 to 4.0 millimeters.

14. The blade of claim 13, made of either stainless steel or a titanium alloy.

15. The blade of claim 14, including a coating chosen from the group consisting of titanium nitride, titanium carbide, titanium carbide-nitride, chrome, aluminum oxide, boron nitride, silicon carbide and silicon nitride.

16. The blade of claim 13, made of stainless steel.

17. The blade of claim 13, made of a material chosen from the group consisting of diamond, sapphire, ruby, cubic zirconia, and pure or composite ceramics.

* * * * *